(12) United States Patent
Sjögren

(10) Patent No.: US 6,548,680 B1
(45) Date of Patent: Apr. 15, 2003

(54) PROCESS FOR THE PRODUCTION OF N-PROTECTED AZETIDINE-2-CARBOXYLIC ACIDS (AZEOHS)

(75) Inventor: Magnus Sjögren, Stockholm (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/402,864

(22) PCT Filed: Aug. 27, 1999

(86) PCT No.: PCT/SE99/01470

§ 371 (c)(1),
(2), (4) Date: Oct. 13, 1999

(87) PCT Pub. No.: WO00/12473

PCT Pub. Date: Mar. 9, 2000

(30) Foreign Application Priority Data

Sep. 1, 1998 (SE) ................................................ 9802939

(51) Int. Cl.⁷ ............................................ C07D 205/04
(52) U.S. Cl. ....................................................... 548/953
(58) Field of Search .......................................... 548/953

(56) References Cited

FOREIGN PATENT DOCUMENTS

| EP | 669 317 | 8/1995 |
|---|---|---|
| JP | 49-14457 | 7/1974 |
| JP | 49-14457 | 8/1974 |
| WO | 94/29336 | 12/1994 |
| WO | 97/02241 | 1/1997 |
| WO | 97/41084 | 11/1997 |
| WO | 98/02417 | 1/1998 |
| WO | 98/02568 | 1/1998 |

OTHER PUBLICATIONS

Yokoyama et al, "The Decomposition Product of Ethyl . . ." Bulletin of the Chemical Society of Japan, vol. 46, pp. 699–700 (1973).

Fowden, L., "Azetidine–2–carboxylic Acid: . . ." vol. 64, pp. 323–332 (1956).

Translation of PCT EP95/02135.

Rodebaugh et al.; "Resolution of DL–Azetidine–2–carboxylic Acid"; Communication to the Editor; J. Heterocyclic Chem., 6, pp. 993–994 (1969).

*Primary Examiner*—Mark L. Berch
(74) *Attorney, Agent, or Firm*—Nixon & Vanderhye

(57) ABSTRACT

There is provided a process for the production of a N-protected azetidine-2-carboxylic acid, which process comprises the steps of: (a) addition of base to an aqueous solvent comprising an organic acid addition salt of an azetidine-2-carboxylic acid; and (b) addition of protecting agent to the resultant reaction mixture.

7 Claims, No Drawings

PROCESS FOR THE PRODUCTION OF N-PROTECTED AZETIDINE-2-CARBOXYLIC ACIDS (AZEOHS)

FIELD OF THE INVENTION

This invention relates to a novel process for the production of protected azetidine-2-carboxylic acids (AzeOHs).

PRIOR ART

L-Azetidine-2-carboxylic acid (L-AzeOH) is known to be useful in the synthesis of inter alia high molecular weight polypeptides and in particular as an analogue of the well known amino acid proline.

The resolution of enantiomerically pure AzeOH, and derivatives thereof, has been described in J. Heterocyclic Chem. (1969) 6, 993, Japanese Patent Application No. 14457/74, Bull. Chem. Soc. Jpn. (1973) 46, 699, Biochem. J. (1956) 64, 323, as well as international patent applications WO 97/02241, WO 97/41084, WO 98/02568 and WO 98/02417.

In the synthesis of peptides, it is often desirable to protect chemically the amino group or the carboxylic acid group of an amino acid-based component before undertaking a peptide coupling reaction. As with all chemical processes, if this can be achieved in a manner which is convenient, and which minimises the necessity for extensive work up before carrying out subsequent reaction steps, this would be advantageous.

Following the synthesis, or resolution, of an amino acid such as AzeOH, the skilled person would typically expect that it would be necessary to isolate the compound (e.g. in an enantiomerically enriched form), before carrying out a coupling, or protection, reaction. This is in order to obtain as high a yield of the ultimate coupled, or protected, compound as possible.

Surprisingly, we have found that N-protected AzeOH, and derivatives thereof, may be obtained efficiently, and in a good yield, without the need to isolate the free amino acid, from certain reaction mixtures in which the latter has been formed.

DESCRIPTION OF THE INVENTION

According to a first aspect of the invention there is provided a process for the production of a N-protected AzeOH, which process comprises the steps of: (a) displacement of organic acid from an organic acid addition salt of an AzeOH by addition of base to an aqueous solvent comprising that salt; followed by (b) protection of the AzeOH by addition of an amine protecting agent to the resultant reaction mixture, which process is referred to hereinafter as "the process of the invention".

Organic acid addition salts of AzeOHs which may be mentioned include those of tartaric acid. Resolutions of AzeOH with tartaric acid, and the preparation of AzeOH-tartrate salts, are described in international patent applications WO 97/02241 and WO 97/41084.

In the process of the invention, the aqueous solvent comprises (i.e. includes) the organic acid addition salt before the displacement step (a) is carried out. The term "aqueous solvent" will be understood by those skilled in the art to include any monophasic or multiphasic solvent mixture in which water is present, for example in an amount of greater than 50%, more preferably greater than 75%, particularly greater than 90% and especially greater than 95% (expressed as a percentage of the total volume of solvent(s)). We prefer that the aqueous solvent is monophasic and/or consists essentially of water. By "consists essentially of water" we include that the solvent is at least 99% pure (e.g. deionised) water.

We prefer that the organic acid addition salt is at least 95% dissolved in the aqueous solvent prior to carrying out the displacement step (a) above (i.e. base is added to an aqueous solution of salt).

Organic acid addition salts of AzeOHs may used in the process of the invention in a form in which the carboxylic acid functionality is protected or, preferably, unprotected. Suitable protecting groups for carboxylic acid include $C_{1-6}$ alkyl or benzyl.

Organic acid addition salts of AzeOHs that may employed in the process of the invention may also include those in which the 3- and/or the 4-position of the AzeOH is substituted by one or more groups, such as $C_{1-4}$ alkyl, $C_{1-4}$ alkoxy, halo (F, Cl, Br or I), aryl (e.g. phenyl) or aryl-$C_{1-6}$-alkyl (e.g. benzyl). However, we prefer that salts of unsubstituted AzeOHs (e.g. AzeOH) are employed.

Organic acid addition salts of D- or, preferably, L-AzeOH, or mixtures (including the racemic mixture) of the two enantiomers may be employed in the process of the invention. Preferred organic acid addition salts are diastereomerically enriched AzeOH-tartrate salts, particularly L-AzeOH-D-tartrate. By "diastereomerically enriched AzeOH-tartrate salt", we include AzeOH-tartrate salts (e.g. L-AzeOH-D-tartrate or D-AzeOH-L-tartrate) with a diastereomeric excess of greater than 40%.

Suitable bases for use in the displacement step include those which will displace the organic acid from the AzeOH, will not displace any carboxylic acid protecting group which is employed, will not react chemically with the AzeOH or the organic acid, and will not give rise to stereochemical changes in the AzeOH molecule (e.g. cause racemization of an enantiomerically-enriched AzeOH, which may be formed following displacement of organic acid). Particularly suitable bases include inorganic bases, such as hydroxides, alkoxides or carbonates of alkali metals (such as Na or K), organic bases, such as common tertiary amine bases (e.g. triethylamine and diisopropylethylamine), or ammonia. A particularly preferred base is potassium hydroxide. Bases can be added in solid form or, preferably, as a liquid (e.g. in solution).

When potassium hydroxide is employed as base, suitable reaction temperatures for the displacement step are in the range 0 to 80° C., particularly 15° to 70° C. and more particularly room temperature to 60° C., though the skilled person will appreciate that this will depend inter alia upon the solvent system which is used.

Following the displacement step (a), displaced organic acid (which may be a salt of the acid) may preferably be removed from the reaction mixture, before carrying out the protection step (b), using techniques which are well known to those skilled in the art (though such removal is not an essential part of the process of the invention).

For example, displaced organic acids (or acid salts) may be removed by crystallisation, which may be achieved by attaining supersaturation in the resultant reaction mixture (e.g. by cooling to supersaturation temperature and/or by solvent evaporation). Final crystallisation temperatures may depend upon the concentration of the organic acid/acid salt in solution, and upon the solvent system which is employed. Suitable temperatures are typically in the range −20 to 10° C., for example −10 to 5° C., preferably −5 to 3° C. Crystallisation can be effected with or without seeding.

Displaced acid/acid salt may be isolated using techniques which are well known to those skilled in the art, for example decanting, filtering or centrifuging.

The protection step (b) is carried out by adding the appropriate protecting agent to the aqueous solvent containing the AzeOH from the displacement step (whether displaced acid is removed or otherwise).

Base is preferably added to the reaction mixture in order to facilitate the protection. Base may be added at the same time as, after, or, preferably, prior to, addition of the protecting agent. Suitable bases include inorganic bases, such as hydroxides, alkoxides or carbonates of alkali metals (such as Na or K), organic bases, such as common tertiary amine bases (e.g. triethylamine and diisopropylethylamine), or ammonia.

Suitable protecting agents include those that will provide a protecting group which is suitable for the protection of an amino functionality, such as a benzyloxycarbonyl (Cbz) group, a 2-trimethylsilylethoxycarbonyl (Teoc) group, a 4-methoxyphenacylcarbonyl (Phenoc) group, a 2,2,2-trichloroethylcarbonyl (Troc) group, a 2,7-di-t-butyl-(10,10-dioxo-10,10,10-tetrahydrothioxanthyl)methylcarbonyl (DBD-Tmoc) group, or, particularly, a tert-butyloxycarbonyl (Boc) group. Suitable protecting agents therefore include di-tert-butyldicarbonate. Protecting agents may be added in appropriate quantities, which may readily be determined or estimated by those skilled in the art. See, for example, *Int. J. Peptide Protein Res.*, 21, 227 (1983).

As will be appreciated by those skilled in the art, protecting agent may be added in an appropriate amount to the reaction mixture, in an appropriate amount of an appropriate solvent. When the protecting agent is di-tert-butylcarbonate, suitable solvents include acetone, iso-propylacetate, toluene, acetonitrile, ethyl acetate, butyl acetate, methylene chloride, chloroform, benzene as well as ethers (e.g. tetrahydrofuran). Preferred solvents include acetone, iso-propylacetate, ethyl acetate, butyl acetate, methylene chloride, acetonitrile, tetrahydrofuran and, especially, toluene, Appropriate amounts of such solvents may determined non-inventively.

Suitable temperatures at which the protection step may be carried out will depend upon factors such as the protecting agent which is employed, the solvent system that is used, and the relative amounts of the reactants, and can be determined non-inventively. For example, when the protecting agent is di-tert-butyldicarbonate, suitable reaction temperatures are in the range room temperature (e.g. 20° C.) to 40° C.

The N-protected AzeOH may be isolated and, if desired, purified, using techniques which will be well known to those skilled in the art, including those described hereinafter.

The N-protected AzeOH formed by way of the process of the invention may be utilised in a subsequent peptide coupling reaction. The formed N-protected AzeOH may be deprotected (at the N-atom and/or, if a carboxylate protecting group is present, at the O-atom) and the resultant compound reacted with a compound comprising an amino group and/or a compound comprising a carboxylate group. For example, a N-protected AzeOH, with a free carboxylate group can be reacted with an amidinobenzylamine, a hydroxyamidinobenzylamine, or a similar benzylamine containing a substituent on the benzene ring that can be converted into an amidino group or a hydroxyamidino group using standard techniques (e.g. a cyano group). Preferred such benzylamines include those substituted in the para-position with an amidino, a hydroxyamidino, or a group (e.g. cyano) which is convertible into amidino or hydroxyamidino, and especially includes such para-substituted benzylamines which are otherwise unsubstituted. The N-protecting groups on the resultant coupled compound can then be removed, and the resultant deprotected compound subjected to a further peptide coupling reaction, in accordance with techniques that will be well known to those skilled in the art.

The process of the invention possesses the surprising advantage that N-protected AzeOHs may be obtained from the corresponding AzeOH without the extra process step of isolating the unprotected (at the N-position) amino acid.

Further, the process of the invention may have the advantage that N-protected AzeOHs may be prepared in higher yields, in less time, more conveniently, and at a lower cost, than when prepared in processes described in the prior art.

The invention is illustrated, but in no way limited, by the following examples.

EXAMPLE 1
Preparation of L-AzeOH in Aqueous Solution

L-AzeOH-D-tartrate (14.0 g; 56 mmol; prepared analogously to the methods described in international patent application WO 97/02441) was added to water (17 mL) at room temperature. The mixture was heated to 60° C. and an additional amount of water (9 mL) was added to completely dissolve the L-AzeOH-D-tartrate. KOH (10.8 mL; 5.7 M) was added over 7 minutes to resultant the yellowish solution. The reaction mixture was then left to cool at room temperature. It was left at this temperature overnight. The reaction mixture was then cooled on ice for 7 h. Potassium hydrogen tartrate crystallised and was filtered off. The filtration gave potassium hydrogen tartrate as white solid (9.5 g; 91%) and a slightly yellowish aqueous solution containing liberated L-AzeOH. The latter was used in the next step without further characterisation.

EXAMPLE 2
Preparation of N-tert-Butyloxycarbonyl-AzeOH

KOH (3.8 g; 58 mmol) was added to the slightly yellowish water solution containing L-AzeOH (6.0 g; 56 mmol) from Example 1 above, over 15 minutes. The solution was cooled to 17° C. and di-tert-butyldicarbonate (14.9 g; 65 mmol) dissolved in toluene (6 mL) was added over 10 minutes. The reaction mixture was stirred until >95% conversion was reached (HPLC). The pH was adjusted to 12±0.5 with NaOH (aq; 50%) and the two phases were separated. The organic phase was extracted a second time with water (5 mL). The aqueous phases were combined, and HCl (aq) was added until the pH reached 1.8–2.5. The aqueous phase was extracted twice with ethyl acetate (17 mL). The organic phase was evaporated which gave white crystals of tert-butyloxycarbonyl protected AzeOH (9.2 g; 85% yield from L-AzeOH-D-tartrate).

mp 106.2° C.

$^1$H NMR (200 MHz; CDCl$_3$) δ1.45 (9H, s), 2.46 (2H, d), 3.91 (2H, t), 4.75 (1H, t), 11.27 (1H, s)

What is claimed is:

1. A process for the production of a N-protected azetidine-2-carboxylic acid, which process comprises the steps of: (a) addition of base to an aqueous solvent comprising an organic acid addition salt of an azetidine-2-carboxylic acid; and (b) reacting the azetidine-2-carboxylic acid with protecting agent.

2. A process as claimed in claim 1, characterised in that the organic acid is a tartaric acid.

3. A process as claimed in claim 2, characterised in that the tartaric acid is D-tartaric acid.

4. A process as claimed in claim 1, wherein the azetidine-2-carboxylic acid is azetidine-2-carboxylic acid.

5. A process as claimed in claim 4, characterised in that the azetidine-2-carboxylic acid is L-azetidine-2-carboxylic acid.

6. A process as claimed in claim 1, wherein the salt is L-azetidine-2-carboxylic acid-D-tartrate.

7. A process as claimed in claim 1, wherein the protecting agent provides a tert-butyloxycarbonyl group.

* * * * *

UNITED STATES PATENT AND TRADEMARK OFFICE
CERTIFICATE OF CORRECTION

PATENT NO.    : 6,548,680 B1　　　　　　　　　　　　　　　　　　　　　　　　　　Page 1 of 1
DATED         : April 15, 2003
INVENTOR(S)   : Sjogren, Magnus It is certified that error appears in the above-identified patent and that said Letters Patent is hereby corrected as shown below:

<u>Column 4,</u>
Line 62, after "acid", please insert -- formed in step (a) --.

Signed and Sealed this

Twenty-fifth Day of November, 2003

JAMES E. ROGAN
*Director of the United States Patent and Trademark Office*